United States Patent
Choi et al.

(10) Patent No.: US 9,212,378 B2
(45) Date of Patent: Dec. 15, 2015

(54) METHOD OF AMPLIFYING DNA FROM RNA IN A SAMPLE

(71) Applicant: Samsung Electronics Co., Ltd., Suwon-si, Gyeonggi-do (KR)

(72) Inventors: Ko-bong Choi, Osan-si (KR); Joo-won Rhee, Yongin-si (KR); Sea-hee Kim, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 26 days.

(21) Appl. No.: 13/856,301

(22) Filed: Apr. 3, 2013

(65) Prior Publication Data

US 2014/0057322 A1 Feb. 27, 2014

(30) Foreign Application Priority Data

Aug. 27, 2012 (KR) .......... 10-2012-0093887

(51) Int. Cl.
*C12P 19/34* (2006.01)
*C12Q 1/68* (2006.01)

(52) U.S. Cl.
CPC ............... *C12P 19/34* (2013.01); *C12Q 1/6844* (2013.01)

(58) Field of Classification Search
CPC ........... C12Q 1/6844; C12Q 2521/107; C12Q 2525/121; C12Q 2525/191; C12Q 2531/125; C12P 19/34

USPC ......................................................... 435/91.2
See application file for complete search history.

(56) References Cited

U.S. PATENT DOCUMENTS

| | | | |
|---|---|---|---|
| 6,124,120 A | 9/2000 | Lizardi | |
| 6,287,825 B1 | 9/2001 | Weissman et al. | |
| 6,372,434 B1 * | 4/2002 | Weissman et al. | 435/6.13 |
| 6,617,137 B2 | 9/2003 | Dean et al. | |
| 7,320,860 B2 | 1/2008 | Landegren et al. | |
| 7,615,625 B2 * | 11/2009 | Auerbach | 536/24.3 |
| 7,790,388 B2 | 9/2010 | Landegren et al. | |
| 2006/0188893 A1 * | 8/2006 | Kumar et al. | 435/6 |
| 2009/0111706 A1 * | 4/2009 | Sparks et al. | 506/9 |
| 2011/0230358 A1 * | 9/2011 | Rava | 506/7 |

OTHER PUBLICATIONS

Lamm et al., Multimodal RNA-seq Using Single-Strand, Double-Strand, and CircLigase-Based Capture Yields a Refined and Extended Description of the *C. elegans* Transcriptome, *Genome Research*, 21: 265-275 (2011), published online Dec. 22, 2010.

* cited by examiner

*Primary Examiner* — Cynthia B Wilder
(74) *Attorney, Agent, or Firm* — Leydig, Voit & Mayer, Ltd.

(57) ABSTRACT

A method of amplifying RNA in a sample and a method of amplifying a pool of RNA is provided. Gene loss and amplification bias may be reduced using the methods. Also, directionality may be preserved in the amplified RNA. The methods may be applied in sequence analysis as well as in general molecular diagnostic areas.

20 Claims, 5 Drawing Sheets

SEQUENCE LISTING

```
<160> NUMBER OF SEQ ID NOS: 9

<210> SEQ ID NO 1
<211> LENGTH: 40
<212> TYPE: DNA
<213> ORGANISM: Artificial Sequence
<220> FEATURE:
<223> OTHER INFORMATION: Synthetic

<400> SEQUENCE: 1
ttaatacgac tcactatagg gatggaatat ttccagcaaa                              40

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
tggtgattgg tttatttctt aa                                                 22

<210> SEQ ID NO 3
<211> LENGTH: 40
<212> TYPE: DNA
<213> ORGANISM: Artificial Sequence
<220> FEATURE:
<223> OTHER INFORMATION: Synthetic

<400> SEQUENCE: 3
ttaatacgac tcactatagg caggaaacga taagccatta                              40

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
aggagtaggt gccaaatc                                                      18

<210> SEQ ID NO 5
<211> LENGTH: 39
<212> TYPE: DNA
<213> ORGANISM: Artificial Sequence
<220> FEATURE:
<223> OTHER INFORMATION: Synthetic

<400> SEQUENCE: 5
ttaatacgac tcactatagg gatccatgag ttaaagcag                               39

<210> SEQ ID NO 6
<211> LENGTH: 18
<212> TYPE: DNA
<213> ORGANISM: Artificial Sequence
<220> FEATURE:
<223> OTHER INFORMATION: Synthetic

<400> SEQUENCE: 6
```

```
gcacttctga tgttttca                                                     18

<210> SEQ ID NO 7
<211> LENGTH: 48
<212> TYPE: DNA
<213> ORGANISM: Artificial Sequence
<220> FEATURE:
<223> OTHER INFORMATION: Synthetic

<400> SEQUENCE: 7
ggttcagcag gaatgccgag gcggccgcac acgacgctct tccgatct                    48

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
acacgacgct cttccgatct                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
ctcggcattc ctgctgaacc                                                   20
```

METHOD OF AMPLIFYING DNA FROM RNA IN A SAMPLE

CROSS-REFERENCE TO RELATED APPLICATIONS

This application claims the benefit of Korean Patent Application No. 10-2012-0093887, filed on Aug. 27, 2012, in the Korean Intellectual Property Office, the disclosures of which are incorporated herein in their entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,874 Byte ASCII (Text) file named "712211_ST25.txt," created on Apr. 3, 2013.

BACKGROUND

1. Field

The present disclosure relates to a method of amplifying RNA from a sample and a method of amplifying a pool of RNAs in a sample.

2. Description of the Related Art

Amplification of a small amount of RNA obtained from a specific biological sample can be the most fundamental and important step in a genetic analysis of the sample. Transcriptome analytic methods, quantitative analysis of RNA (e.g., gene-expression analysis) and qualitative analysis of RNA (e.g., RNA-sequence analysis) are the main methods used to analyze RNA from biological tissues. In each of these methods, amplifying the RNA to a sufficient amount without modification allows for further accurate and meaningful analysis.

A conventional method of amplifying an RNA pool for transcriptome analysis includes reverse transcribing linear RNA to produce single-stranded DNA using oligo dT primers or primers with random sequences, displacing the single-stranded DNA with a double-stranded DNA using random primers, ligating different adapters to a 5'-end and a 3'-end of the double-stranded DNA, and preparing a complementary DNA (cDNA) library by amplifying the DNA.

According to the conventional method, cDNA conversion efficiency may differ depending on the RNA used in the reverse transcription process because, for example, the RNA may have various primary or secondary structures. Also, reverse transcribed DNA corresponding to some expressed genes may be lost due to improper adapter ligation.

Moreover, the conventional method may require reversing the sequence of amplified RNA (or cDNA) to obtain the original RNA sequence direction after sequence analysis because the ligated adapters cannot recognize the directionality (i.e., the adapters do not distinguish between the reverse transcribed cDNA ends corresponding to the 5'-ends and 3'-ends) of the original RNA.

In addition, amplification bias may occur during an amplification process of RNA according to the conventional method. In particular, a polymerase chain reaction (PCR) using a specific sequence may result in biased amplification of some reverse transcribed target DNAs more than others, depending on the sizes and characteristics of the target sequences. A multiple displacement amplification (MDA) using primers of random sequences may also result in different bonding efficiencies of primers depending on the target(s) due to the diversity of structures and sequences of the single-stranded DNAs. Therefore, amplification bias resulting in different degrees of amplification of different genes may be observed in conventional MDA methods.

Methods are desired to reduce loss of genes and/or amplification bias during preparation of cDNA libraries. Methods are desired that allow directionality of the original RNA to be retained in the amplified RNA.

SUMMARY

Provided is a method of amplifying RNA from a sample. Also provided is a method of amplifying a pool of RNAs in a sample, e.g., to make a pool of cDNA. As used herein, amplifying RNA refers to the amplification of RNA or DNA that provides sequence information regarding RNA from a sample Additional aspects will be set forth in part in the description which follows and, in part, will be apparent from the description, or may be learned by practice of the presented embodiments.

According to one aspect of the present invention, a method of amplifying RNA in a sample includes forming an adapter nucleic acid-RNA fusion construct by ligating the RNA to an adapter nucleic acid; forming a circular adapter nucleic acid-RNA fusion construct by self-ligating the adapter nucleic acid-RNA fusion construct; and forming an amplified product by incubating the circular adapter nucleic acid-RNA fusion construct, primers of a sequence that is the same as a continuous nucleotide sequence selected from one strand of the adapter nucleic acid, and primers including a sequence that is complementary to the continuous nucleotide sequence selected from the same strand of the adapter nucleic acid.

BRIEF DESCRIPTION OF THE DRAWINGS

These and/or other aspects will become apparent and more readily appreciated from the following description of the embodiments, taken in conjunction with the accompanying drawings.

FIG. 1 also illustrates the preservation of directionality in the dsDNA library amplification product following treatment with restriction enzyme.

DETAILED DESCRIPTION

Figure 1:
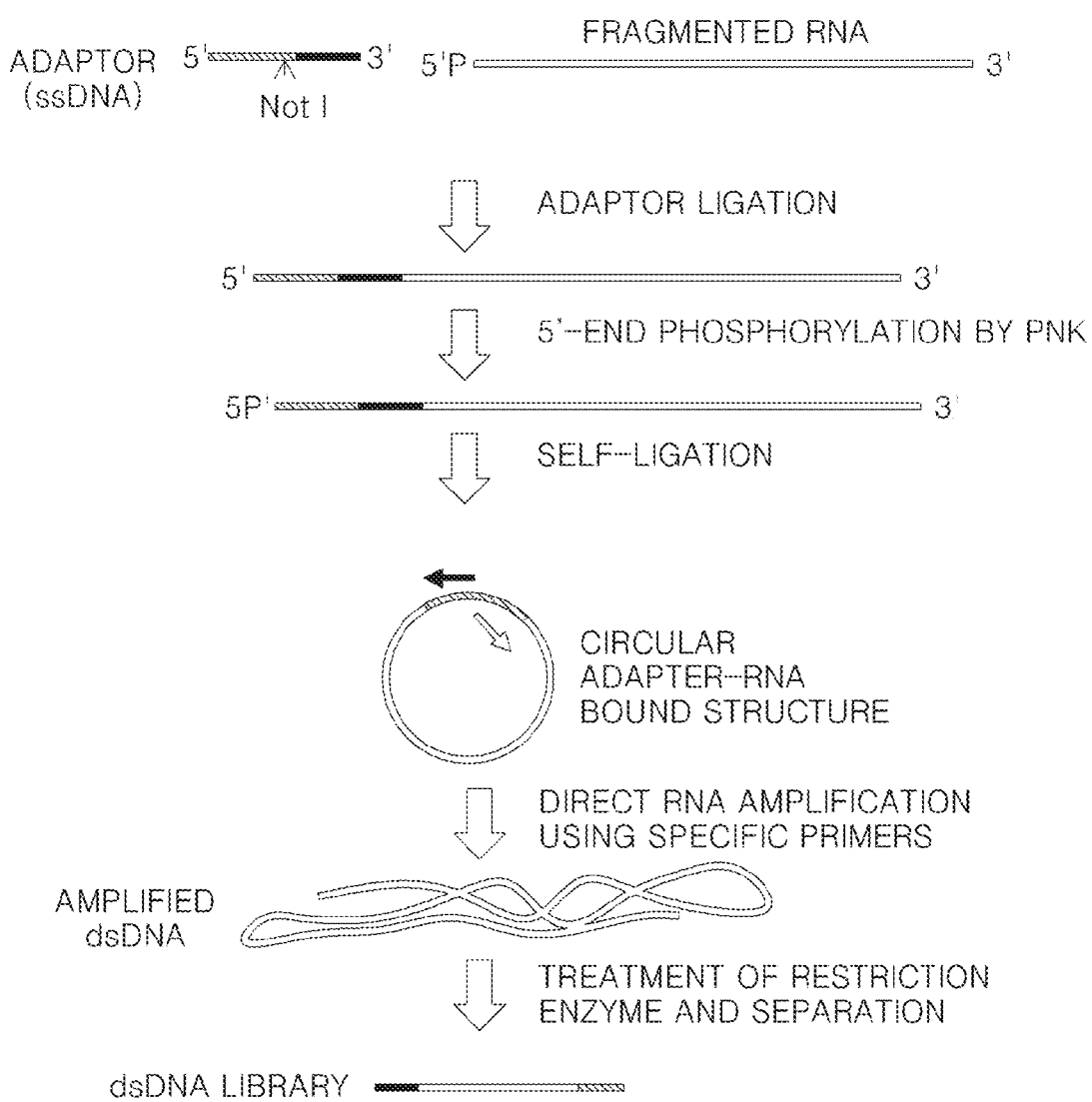
FIG. 1 is a diagram that illustrates an outline of a method of amplifying RNA in a sample using an adapter including a primer sequence for bi-directional amplification or a primer sequence complementary to the a primer sequence for bi-directional amplification.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

According to one aspect, the present invention provides a method of amplifying RNA in a sample that includes forming an adapter nucleic acid-RNA fusion construct by incubating a sample containing RNA and an adapter nucleic acid under ligating conditions; forming a circular adapter nucleic acid-RNA fusion construct by incubating the adapter nucleic acid-RNA fusion construct under self-ligating conditions; and amplifying RNA by incubating the circular adapter nucleic acid-RNA fusion construct, one or more primers that includes a continuous nucleotide sequence selected from a first strand of the adapter nucleic acid, and one or more primers including a sequence that is complementary to a continuous nucleotide sequence selected from the first strand of the adapter nucleic acid. The step of amplifying RNA forms an amplification product.

The method includes forming of an adapter nucleic acid-RNA fusion construct by incubating a sample containing RNA, and an adapter nucleic acid.

The RNA may be natural, synthesized, or semi-synthesized RNA. For example, RNA may be mRNA, tRNA, rRNA, microRNA, small interfering RNA (siRNA), or anti-sense RNA.

The sample containing RNA may be a biological sample, RNA separated (e.g., isolated) from the biological sample, or a fraction thereof. The sample may also include a combination of the foregoing samples containing RNA. The biological sample may include viruses, or a sample derived from an organism. For example, the sample may be at least one selected from the group consisting of blood, saliva, urine, stool, tissue, cells, and biopsy material. The sample may be a preserved biological sample or RNA separated therefrom. The preservation may be done by using a well-known method. The preservation may be done for 1 year or more, for example, 1 year to 10 years. The RNA may be derived from tissue preserved at a freezing temperature or formalin-fixed paraffin-embedded (FFPE) tissue that can be, for example, preserved at room temperature. The method to separate RNA from a biological sample may be a well known method. For example, a Trizol method may be used. The sample may include a transcriptome or a fraction thereof from a cell or cell type.

The sample may include degraded product of the RNA separated from the biological sample. The sample may include the RNA separated from the sample of FFPE tissue. Natural mRNA of eukaryotic cells has a 5'-cap structure and a 3'-poly(adenylate) sequence. However, mRNA may be degraded during preservation and handling of a biological sample or mRNA separated from the biological sample. In this case, the separated and/or degradedRNA may not have a 5'-cap structure and a 3'-poly(adenylate) sequence, which is a structure of natural mRNA. The mRNA may include any other structures that are not characteristic of the natural mRNA structure. For example, the sample may include one or more structures selected from the group consisting of RNA having 5'-terminal cap and 3' terminal-OH; RNA having 5'-terminal cap and 3'-terminal monophosphate; RNA having 5'-terminal OH and 3'-terminal monophosphate; RNA having 5'-terminal OH and 3'-terminal OH; RNA having 5'-terminal monophosphate and 3'-terminal OH; and RNA having 5'-terminal monophosphate and 3'-terminal monophosphate. A 5'-terminal cap structure can be 7-methylguanylate linked to 5'-terminus of the RNA through a triphosphate linkage or a 5'-terminal cap structure can be guanylate, which is a breakdown product of 7-methylguanylate, linked to 5'-end of the RNA through a triphosphate linkage. The 3'-OH and/or 2'-OH of terminal guanylate in a 5'-cap structure and the 2'-OH of the first and second nucleotides from the 5'-terminus of RNA transcripts may be methylated. The method may further include removing the 5'-cap structure of RNA in the sample, or dephosphorylating the 3'-end of RNA in the sample by phosphatase treatment. As used herein, "5'-end" and "3'-end" refer to the 5'-terminus and 3'-terminus of a polynucleotide strand, respectively.

The adapter nucleic acid may be DNA or RNA. Also, the adapter may be single-stranded or double-stranded. For example, the adapter nucleic acid may be an oligonucleotide comprising SEQ ID NO: 7. The adapter nucleic acid may include a sequence that is the same as a primer sequence, a sequence that is complementary to a primer sequence, or a combination of both.

The adapter nucleic acid may further include a restriction enzyme recognition site. The restriction enzyme recognition site and the restriction enzyme thereof and may be appropriately selected by one of ordinary skill in the art. The term "restriction enzyme" refers to endonuclease that recognizes a specific sequence and cleaves double-stranded chains of DNA. The term "restriction enzyme recognition site" refers to a short DNA sequence that is recognized by the restriction enzyme to catalyze endonuclease cleavage in the DNA. For example, the restriction enzyme may be NotI. When the adapter nucleic acid including a restriction enzyme recognition site is used to amplify RNA and to form an amplification product (e.g., cDNA), the amplification product may be cleaved by the restriction enzyme that recognizes the restriction enzyme recognition site in the adapter. The amplification product may allow for the directionality of the original RNA to be retained and/or determined after the restriction enzyme cleaves the amplification product. The adapter nucleic acid may further include a sequence that is the same as any one primer among a primer set and a sequence that is complementary to another primer among the primer set.

The adapter nucleic acid-RNA fusion construct refers to an adapter nucleic acid that is bound to any one of two ends of RNA. The adapter nucleic acid-RNA fusion construct may be linear. For example, the adapter nucleic acid and RNA may be bound to the 5'-terminus of the RNA, the adapter nucleic acid may be bound to the 3' terminus of the RNA, or RNA-adapter nucleic acid fusion construct may include adapter nucleic acid at both the 5' and 3' termini.

The forming of the adapter nucleic acid-RNA fusion construct may include incubating the adapter nucleic acid and the RNA in the presence of ligase under conditions suitable for ligation.

The ligase may be RNA ligase. The RNA ligase may be an enzyme known in the art. For example, the RNA ligase may be T4 RNA ligase 1, T4 RNA ligase 2, CIRCLIGASE™ I, CIRCLIGASE™ II, Mth RNA ligase, or a combination thereof. The T4 RNA ligase may template-independently catalyze formation of a phosphodiester linkage between 5'-phosphate and 3'-OH. The T4 RNA ligase is ATP dependent and active with respect to a wide range of temperament including RNA, DNA, oligo ribonucleotide, oligo deoxyribonucleotide, and a plurality of nucleotide inducing agents.

The incubation may be performed under appropriate conditions suitable for ligation. The suitable conditions for ligation may be appropriately selected by one of ordinary skill in the art according to the selected enzyme. For example, the incubation may be performed in the presence of a T4 RNA ligase 1× reaction buffer for a sufficient amount of time to form adapter nucleic acid-RNA fusion construct.

The adapter or the adapter nucleic acid-RNA fusion construct may be incubated in the presence of nuclease. The nuclease may be, for example, an exonuclease. Suitable conditions for incubation with exonuclease may include, for example, reaction buffers suitable for ligation.

The method may further include forming a circular adapter nucleic acid-RNA fusion construct by incubating the adapter nucleic acid-RNA fusion construct under conditions suitable for intermolecular or intramolecular self-ligation.

The adapter nucleic acid-RNA fusion construct is as described above.

The circular adapter nucleic acid-RNA fusion construct refers to the adapter nucleic acid-RNA fusion construct that is circularized. For example, the circular adapter nucleic acid-RNA fusion construct may be formed by intramolecular ligation or self-ligation of the adapter nucleic acid-RNA fusion construct in a molecule. For example, the circular adapter nucleic acid-RNA fusion construct may be circularized by linking 5'-end and 3'-end of the adapter nucleic acid-RNA fusion construct molecule.

The forming of the circular adapter nucleic acid-RNA fusion construct may include incubating the structure in the presence of ligase. The ligase may be RNA ligase or DNA ligase. The RNA ligase is as described above. The DNA ligase may be an enzyme known in the art. For example, the DNA ligase may be T4 DNA ligase, T3 DNA ligase, T7 DNA ligase, E. Coli DNA ligase, AMPLIGASE® DNA ligase, CIRCLIGASE™ ssDNA ligase, or a combination thereof. The CIRCLIGASE™ ssDNA ligase is a heat-stable ATP-dependent ligase that catalyzes intramolecular ligation (e.g., circularization) of a single-stranded DNA template having 5'-phosphate and 3'-OH. CIRCLIGASE™ and AMPLIGASE® are available from Epicentre, (Madison, Wis.).

The incubation may be performed under appropriate conditions for self-ligation. The condition suitable for self-ligation may be appropriately selected by one of ordinary skill in the art according to the selected enzyme. For example, the incubation may be performed in the presence of a CIRCLIGASE™ ssDNA ligase 1× reaction buffer. The incubation may be performed in the presence of 1M of betaine. The incubation may be performed in the presence of 2.5 mM of $MnCl_2$. For example, the incubation may be performed at a temperature of 60° C. for one hour.

The forming of the adapter nucleic acid-RNA fusion construct and the forming of the circular adapter nucleic acid-RNA fusion construct may be performed in one incubation step. The single incubation step, may optionally further include exonuclease treatment of the adapter or adapter nucleic acid-RNA fusion construct in the incubated reaction mixture to remove adapters that were not ligated.

The method of amplifying RNA may further include incubating the circular nucleic acid-RNA fusion construct with one or more primers of a sequence that is the same as a continuous nucleotide sequence selected from one strand of the adapter nucleic acid, and one or more primers including a sequence that is complementary to a continuous nucleotide sequence selected from the same strand of the adapter nucleic acid.

The circular adapter nucleic acid-RNA fusion construct is as described above.

The one or more primers of a sequence that is same as a continuous nucleotide sequence selected from one strand of the adapter nucleic acid, and the primers including a sequence that is complementary to a continuous nucleotide sequence selected from the same strand of the adapter nucleic acid may be different oligonucleotides. The term 'primer' refers to oligonucleotides of a single strand that may serve as an initiating point of template-directed DNA synthesis under appropriate conditions (e.g., 4 different nucleoside triphosphates (NTPs) and polymerase reaction enzyme) in an appropriate buffer at an appropriate temperature. An appropriate length of the primer is, for example, from 15 to 35 nucleotides, although the length may vary with respect to various factors, such as a required temperature and use of the primer. A short primer may generally require a relatively lower temperature to form a sufficiently stabilized hybrid composite with a template. The primer may form a double-stranded structure by being hybridized or annealed at one region of the template. Conditions for hybridizing appropriate nucleic acids to form the double-stranded structure are well-known to and/or can be readily determined by one of ordinary skill in the art. The primer may include a sequence that is same as a sequence on the adapter nucleic acid or a sequence that is complementary to the adapter nucleic acid sequence. For example, the primer may include a complementary sequence with respect to a continuous nucleotide sequence selected from one strand of the adapter nucleic acid. Also, for example, the primer may include a continuous nucleotide sequence selected from one strand of the adapter nucleic acid. The primers including the sequence that is same as the continuous nucleotide sequence in one strand of the adapter nucleic acid and the primer including the sequence that is complementary a continuous nucleotide sequence in the same strand of the adapter nucleic acid may be designed in the manner that the nucleic acids are extended away from the adapter nucleic acid during the process of amplifying RNA to form amplified product, such as cDNA. For example, the primer sequence may be a sequence that is same as the adapter nucleic acid or complementary to the adapter nucleic acid, as exemplified by thea sequences of SEQ ID NO: 8 or 9, respectively.

The amplifying of the RNA to form an amplification product may include incubating the circular nucleic acid-RNA fusion construct in the presence of polymerase under conditions suitable for nucleic acid amplification (or polymerization).

The polymerase may be DNA polymerase. The DNA polymerase may be, for example, RNA-dependent DNA polymerase. The RNA-dependent DNA polymerase may have strand-displacement DNA polymerase activity. That is, the DNA polymerase may have DNA-dependent DNA polymerase activity as well as reverse transcriptase activity. The DNA polymerase may be Bst DNA polymerase, an exonuclease minus polymerase, HIV reverse transcriptase, pyrophage 3173 DNA polymerase (available from Lucigen, Middleton, Wis.), Tth polymerase, BcaBEST DNA polymerase (available from Takara, Mountain View, Calif.), or a combination thereof. For example, the DNA polymerase may be Bst DNA polymerase (exonuclease minus). The Bst DNA polymerase (exonuclease minus) is 67 kDa *Bacillus stearothermophilus* DNA polymerase protein (a large fragment) with 5'-3' polymerase activity and strand-displacement activity but without 3'-5' exonuclease activity. Also, the Bst DNA polymerase (exonuclease minus) has reverse transcription activity. The Bst DNA polymerase (exonuclease minus) may be used in nucleic acid amplification including isothermal amplification, whole genome amplification, multiple displacement amplification (MDA), or the like.

The incubation may be performed under the appropriate conditions suitable for nucleic acid amplification or polymerization. Conditions suitable for nucleic acid amplification or polymerization may be appropriately selected by one of ordinary skill in the art according to the selected enzyme. The incubation may be performed in the presence of primers. For example, the incubation may be performed in the presence of Bst DNA polymerase 1× reaction buffer (20 mM Tris-HCl (pH 8.8, 25° C.), 10 mM $(NH_4)_2SO_4$, 10 mM KCl, 2 mM $MgSO_4$, 0.1% Triton X-100), 10 mg/ml BSA, 1 µM of a primer set for bi-directional amplification, and 1 unit of Bst DNA polymerase. For example, the incubation may be performed at a temperature of 45° C. for 2 hours.

The term "amplification" or "amplifying" herein refers to increasing a number of DNA copies and includes generation of DNA from RNA. A method for the amplification may be a known method. For the amplification, amplifying DNA from circular RNA may be performed in the presence of primers including a continuous sequence of the nucleic acid adapter or a primer sequence that is complementary to a continuous sequence of the nucleic acid adapter. The amplification method may require thermal cycling or may be performed under isothermal conditions. For example, the amplification method may include polymerase chain reaction (PCR), nucleic acid sequence-based amplification (NASBA), ligase chain reaction (LCR), strand displacement amplification (SDA), multiple displacement amplification (MDA), rolling circle amplification (RCA), or the like. The amplification method may also include a RNA amplification method. For example, the RNA amplification method may include reverse transcription (RT) or reverse transcription-PCR. "PCR" may be a method of amplifying a target nucleic acid from a pair of primers specifically binding to the target nucleic acid using polymerase. For example, the nucleic acid amplification repeats a cycle of denaturation, annealing, and elongation. The term "annealing" may be interchangeably used with the term "hybridization". Also, the amplification may be DNA amplification or RNA amplification. The PCR may be, for example, real-time PCR. The term "real-time PCR (RT-PCR)" may be a method of observing an increase in a PCR product every cycle of the PCR in real-time, and the RT-PCR is a method of analyzing a sample by detection and quantification of a fluorescence material that reacts with the PCR product.

The method of amplifying RNA may further include phosphorylating 5'-end of the adapter nucleic acid-RNA fusion construct using polynucleotide kinase (PNK). The enzyme for phosphorylating 5'-end may be an enzyme known in the art. For example, an enzyme phosphorylating 5'-end may be T4 polynucleotide kinase (T4 PNK) or a variant thereof. Conditions suitable for phosphorylation may be appropriately selected by one of ordinary skill in the art according to the selected PNK enzyme. The phosphorylation may be performed under appropriate conditions suitable for phosphorylating the 5'-end of the adapter nucleic acid-RNA fusion construct. The PNK catalyzes transfer and exchange of a phosphate group at a γ position of ATP to the 5'-OH terminals of polynucleotides (e.g., double- and single-stranded DNA and RNA) and nucleoside 3'-monophosphates. The PNK also may have phosphatase activity that catalyzes removal of a 3'-phosphoryl group from 3'-phosphorylated polynucleotides, deoxynucleoside 3'-monophosphate, and deoxynucleoside 3'-diphosphate. Thus, when PNK is used, phosphorylation of the 5'-terminal OH and removal of the 3'-terminal phosphoryl group may be performed simultaneously or in the same reaction process.

The method may further include sequence analyzing the RNA amplified from the circular adapter nucleic acid-RNA fusion construct.

The method may further include cleaving the amplified RNA (amplification product) with a restriction enzyme recognizing a restriction enzyme recognition site in the adapter nucleic acid. The amplified RNA (amplification product) may indicate and/or retain the directionality of the original RNA in the sample after the restriction enzyme cleaves the amplified RNA (amplification product).

In the method, gene loss in the amplification product may be minimized as the circular adapter nucleic acid-RNA fusion construct is formed. Moreover, the circular nucleic acid-RNA fusion construct can be amplified at once using the primers including the primers of the sequence that is the same as a continuous nucleotide sequence in one strand of the adapter nucleic acid and the sequence that is complementary to a continuous nucleotide sequence in the one strand of the adapter nucleic acid, thus gene loss and amplification bias caused by reverse transcription and DNA amplification may be minimized. Accordingly, the method may be used effectively in the study of gene expression associated with mechanism of diseases and in the development of RNA expression based diagnostic markers. In addition, the amplified RNA (amplification product) may allow for the directionality (5' to 3' orientation) of the original RNA in a sample to be retained and/or determined.

Figure 2:
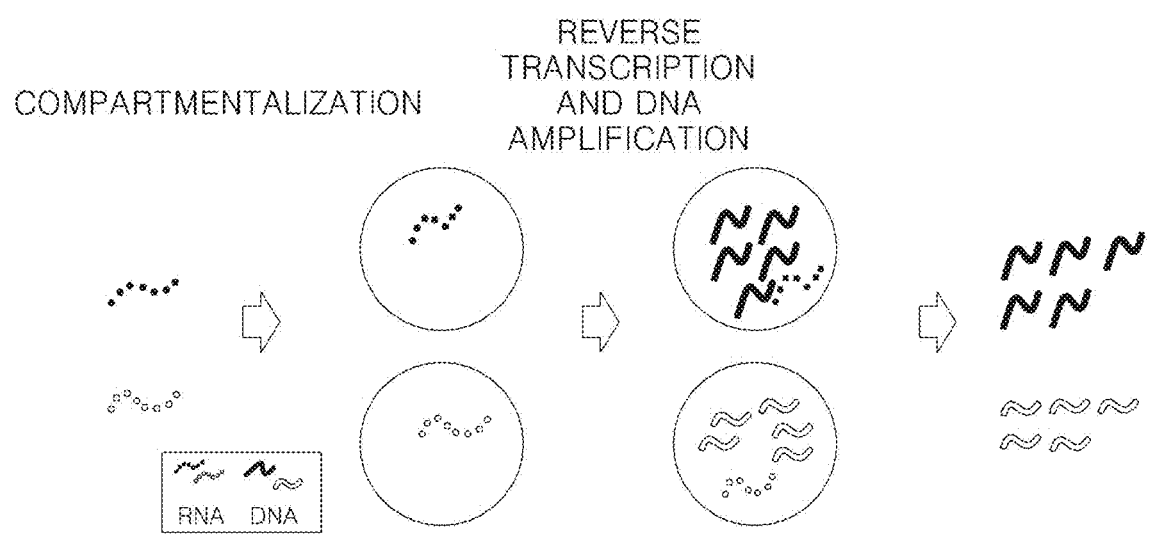
FIG. 2 is a diagram that illustrates an outline of a method of amplifying RNA in a water-in-oil reactor that is compartmentalized.

The method may be performed in a reactor containing microcompartments of water-in-oil emulsions that include aqueous components (FIG. 2). DNA is sufficiently amplified from template RNA or DNA included in each of the microcompartments, and thus the reaction may be continued until space and enzyme function are restricted for any further amplification.

According to another embodiment of the present invention, a method of amplifying an RNA pool in a sample is provided, wherein the method includes forming of a pool of adapter nucleic acid-RNA fusion constructs by incubating the sample including a pool of two or more types of RNA and an adapter nucleic acid under ligating conditions; forming a pool of circular adapter nucleic acid-RNA fusion constructs by incubating the adapter nucleic acid-RNA fusion constructs under self-ligating conditions; and amplifying RNA by incubating together, under conditions suitable for amplification, the pool of circular adapter nucleic acid-RNA fusion constructs, primers of a sequence that is the same as a continuous nucleotide sequence selected from one strand of the adapter nucleic acid, and primers including a sequence that is complementary with the continuous nucleotide sequence selected from one strand of the adapter nucleic acid.

The sample including two or more types of RNA may be the RNA pool. The term "two or more types of RNA" refers to two or more RNAs with different lengths, nucleic acid sequences, and/or structures. For example, even when the two or more types of RNA have the same RNA structure, the RNA molecules with different lengths or sequence compositions from one another may be present in the sample.

The adapter nucleic acid, adapter nucleic acid-RNA fusion construct, conditions suitable for ligation, circular adapter nucleic acid, and conditions suitable for self-ligation are as described above.

The amplifying of the RNA, amplification product, and conditions suitable for amplification or polymerization are as described above.

The amplifying of RNA from the pool of circular adapter nucleic acid-RNA fusion constructs may be used to amplify the pool of RNA in the sample. As the pool of circular adapter nucleic acid-RNA fusion constructs are formed, gene loss may be minimized in the amplification product. Also, as the circular adapter nucleic acid-RNA fusion construct is amplified using one or more primers of a sequence that is the same as a continuous nucleotide sequence in one strand of the adapter nucleic acid, and one or more primers including a sequence that is complementary to a continuous nucleotide sequence in the one strand of the adapter nucleic acid, gene loss and amplification bias caused by reverse transcription and DNA amplification may be minimized. When the RNA in the sample is an RNA pool including two or more types of RNA, the RNA pool may be amplified while minimizing gene loss and amplification bias, and thus a more accurate transcriptome analysis may be enabled. For example, the amplification product from the circular RNA may be used in molecular diagnostics. In addition, the directionality of the original sample RNA may be determined and/or preserved in the amplified RNA. Accordingly, the method may be used in the study of mechanism of action of diseases and the method may be used in the development of diagnostic markers for diseases. For example, the method may be used in molecular diagnostic areas such as sequence analysis, microarray analysis, a fluorescence in situ hybridization (FISH) method, polymerase chain reaction (PCR), reverse transcription-polymerase chain reaction (RT-PCR), transcription mediated amplification (TMA), nucleic acid sequence based amplification (NASBA), rolling circle amplification (RCA), and strand displacement amplification (SDA).

Hereinafter, one or more embodiments will be described in detail with reference to the following examples. However, these examples are not intended to limit the purpose and scope of the invention.

EXAMPLE 1

Preparation of Target RNA 1-1. Preparation of Linear Double-Stranded DNA Fragment Primer pairs below were polymerase chain reacted from two kinds of plasmid vectors, pcDNA3.1 elF2a (Kim et al. *EMBO J.* 2011 10; 30(12):2454-64) and pcDNA3.1 eIF5B (Kim et al. *EMBO J.* 2011 10; 30(12):2454-64), to obtain linear double-stranded DNA fragments.

T7-eIF2A 1252-forward:
(SEQ ID NO: 1)
5'-TTAATACGACTCACTATAGGGATGGAATATTTCCAGCAAA-3',
and eIF2A 1252-reverse:
(SEQ ID NO: 2)
5'-TGGTGATTGGTTTATTTCTTAA-3'.

T7-eIF2A 1421-forward:
(SEQ ID NO: 3)
5'-TTAATACGACTCACTATAGGCAGGAAACGATAAGCCATTA-3',
and eIF2A 1421-reverse:
(SEQ ID NO: 4)
5'-AGGAGTAGGTGCCAAATC-3'.

T7-eIF5B 2889-forward:
(SEQ ID NO: 5)
5'-TTAATACGACTCACTATAGGGATCCATGAGTTAAAGCAG-3',
and -continued eIF5B 2889-reverse:
(SEQ ID NO: 6)
5'-GCACTTCTGATGTTTTCA-3'.

The vectors were reacted with a composition of 1×HS Prime Taq premix (GeNet bio), 0.5 μM of forward primers, 0.5 μM of reverse primers, 10 ng of plasmid vectors, and water. The composition was incubated at a temperature of 94° C. for 10 minutes, followed by thermal circulation that is repeated 30 cycles of 30 seconds at 94° C., 30 seconds at 55° C., and 30 seconds at 72° C., and then the composition was incubated at 72° C. for 5 minutes.

Figure 3:
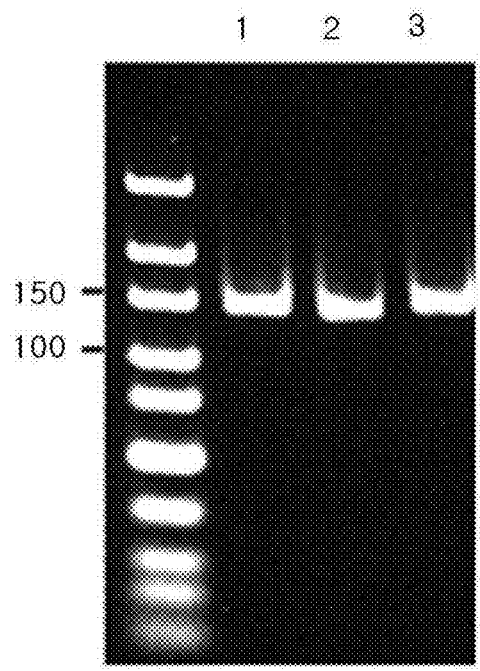
FIG. 3 is an electrophoresis gel image that shows a linear double-stranded DNA obtained according to an embodiment of the present invention.

The obtained PCR products, i.e., linear double-stranded DNA fragments, were confirmed using electrophoresis, and the results are shown in FIG. 3. Lane 1; eIF2A 1252:1372, Lane 2; eIF2A 1421:1539, Lane 3; eIF5B 2889:3010. T7 promoter regions of the obtained DNA fragments were included in 5'-ends, and sizes of the fragments were 121 bp (eIF2A 1252:1372), 118 bp (eIF2A 1421:1539), and 122 bp (eIF5B 2889:3010).

1-2. Preparation of RNA

In vitro transcription was performed on the linear double-stranded DNA fragments obtained in Example 1-1 to obtain mRNA. Specifically, a composition of 100 ng of the linear double-stranded DNA fragments obtained in Example 1-1, 2 μl T7 RNA of polymerase (Invitrogen, Carlsbad Calif.), a 1× reaction buffer (40 mM of Tris-HCl, 6 mM of $MgCl_2$, 10 mM of DTT, and 2 mM of spermidine, pH 7.9 at 25° C.), 7.5 mM of NTPs (ATP, CTP, GTP, and UTP), and water was incubated at 37° C. for 2 hours.

Figure 4:
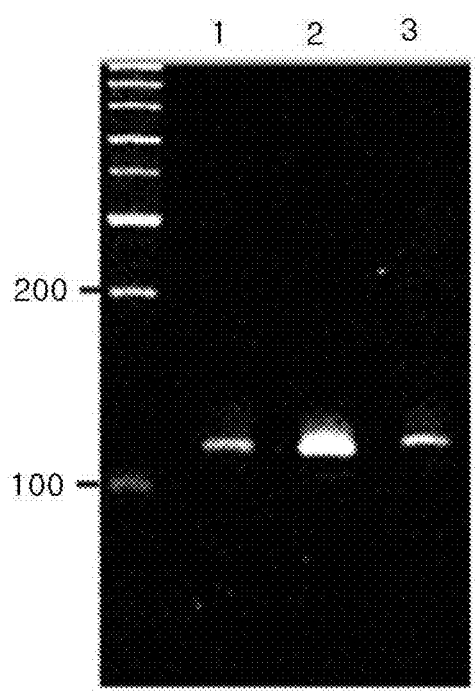
FIG. 4 is an electrophoresis gel image that shows RNA product obtained from the linear double-stranded DNA analyzed in FIG. 3 by in vitro transcription reaction according to an embodiment of the present invention.

The obtained mRNA product was confirmed using electrophoresis, and the results are shown in FIG. 4. Lane 1: eIF2A 1252:1372, Lane 2: eIF2A 1421:1539, Lane 3: eIF5B 2889:3010.

EXAMPLE 2

Ligation of Adapter Nucleic Acid

Each of the mRNA products obtained in Example 1-2 was ligated to the following adapter nucleic acid formed of a single-stranded DNA.

P6 adapter nucleic acid sequence:

(SEQ ID NO: 7)
5'-OH-GGTTCAGCAGGAATGCCGAG<u>GCGGCCG</u>CACACGACGCTCTTCCG

ATCT-3'

The underlined part of the P6 adapter sequence indicates a recognition site for restriction enzyme NotI.

The ligation reaction composition included 100 ng of mRNA obtained in Example 1-2, 6.67 μM of the P6 adapter, 1 μl of RNA 5'-pyrophosphohydrolase (New England Biolabs, Ipswich, Mass.), 1 unit of T4 RNA ligase 1(New England Biolabs), a 1× reaction buffer (50 mM of Tris-HCl, 10 mM of $MgCl_2$, and 1 mM of DTT, at 25° C. at pH 7.9), 0.1 mM of ATP, and water. This composition was incubated at 37° C. for 1 hour.

Next, 1 unit of exonuclease I was added to the composition and it was incubated at 37° C. for another 30 minutes to remove adapters that were not ligated.

Figure 5:
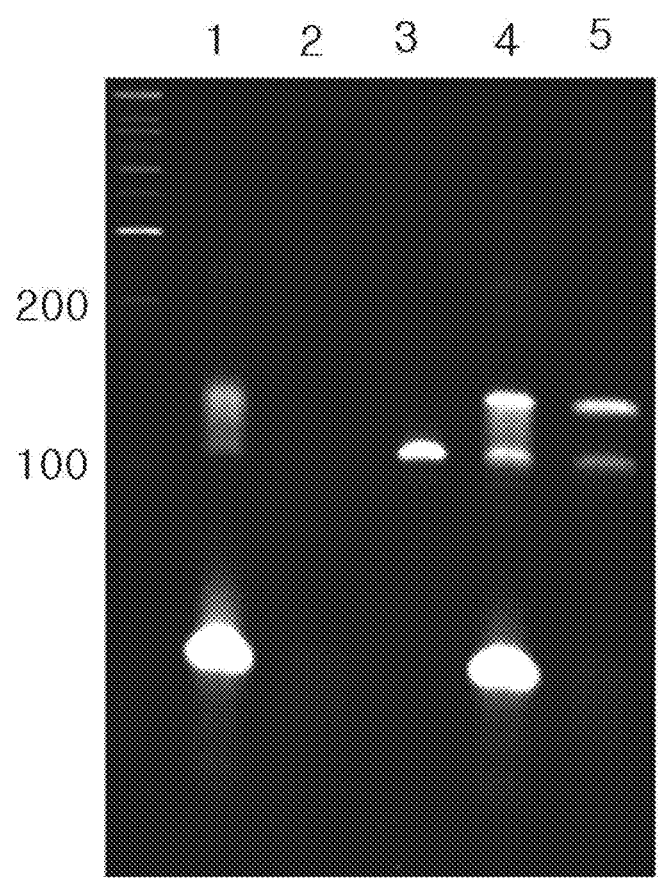
FIG. 5 is an electrophoresis gel image that shows an adapter nucleic acid-RNA fusion construct obtained by ligating a single-stranded adapter nucleic acid to the RNA product analyzed in FIG. 4.

The RNA to which the adapter nucleic acid is ligated can be used to make a circular adapter nucleic acid-RNA fusion construct, as described herein and illustrated in FIG. 1. The ligated DNA adapter-RNA fusion construct obtained from the foregoing ligation and exonuclease reactions was confirmed using electrophoresis, as shown in FIG. 5.

Each of lanes 1-5 in FIG. 5 corresponds to the product of reacting the components listed in each of columns 1-5, respectively, of Table 1 below. In Table 1, an "O" indicates a component that was included in the reaction, and an "X" indicates a component that was not included the reaction. Thus, lanes 1-3 in FIG. 5 show the products of control reactions missing at least one of the components in the ligation reaction described above. Lanes 4 in FIG. 5 shows the product of a control ligation reaction which was not followed by treatment with exonuclease I. The adapter nucleic acid-RNA ligated structure (the DNA-RNA hybrid) product of the ligation and exonuclease reactions described above is shown in FIG. 5, lane 5.

TABLE 1

| | Lane | | | | |
|---|---|---|---|---|---|
| | 1 | 2 | 3 | 4 | 5 |
| Adapter nucleic acid | O | O | X | O | O |
| RNA | X | X | O | O | O |
| RNA ligase 1 | X | X | X | O | O |
| Exonuclease I | X | O | X | X | O |

EXAMPLE 3

Preparation and Amplification of Circular Adapter Nucleic Acid-RNA Fusion Construct 3-1. Preparation of Adapter Nucleic Acid-RNA Fusion Construct A reaction composition containing 100 ng of DNA-RNA hybrid obtained in Example 2, 1 unit of T4 polynucleotide kinase (PNK)(NEB), a 1× reaction buffer (70 mM of Tris-HCl, 10 mM of $MgCl_2$, and 5 mM of DTT, pH 7.6 at 25° C.), and water was incubated at 37° C. for 1 hour to make PNK treated product.

Next, a composition containing 70 ng of the PNK treated product, 100 units of CIRCLIGASE™ II ssDNA ligase (Epicentre), a 1× reaction buffer (0.33 M Tris-acetate (pH 7.5), 0.66 M potassium acetate, and 5 mM DTT), 1M betaine, 2.5 mM $MnCl_2$, and water was incubated at 60° C. for 1 hour to make a circular adapter nucleic acid-RNA construct.

3-2. Amplification of RNA from Circular Adapter Nucleic Acid-RNA Fusion Construct A composition containing circular adapter nucleic acid-RNA fusion construct, 1 unit of Bst DNA polymerase, 1 µM of P6 AmP1 primers (SEQ ID NO: 8), 1 µM P6 of AmP2 primers (SEQ ID NO: 9), a 1× reaction buffer (20 mM of Tris-HCl, 10 mM of $(NH_4)_2SO_4$, 10 mM of KCl, 2 mM of $MgSO_4$, and 0.1% of Triton X-100, pH 8.8 at 25° C.), 10 mg/ml of BSA, and 1.3 mM of dNTPs was incubated at 45° C. for 2 hours.

The nucleic acid sequences of primers P6 AmP1 and P6 AmP2 are as follows.

```
P6 AmP1:
                                   (SEQ ID NO: 8)
5'-ACACGACGCTCTTCCGATCT-3'

P6 AmP2:
                                   (SEQ ID NO: 9)
5'-CTCGGCATTCCTGCTGAACC-3'
```

P6 AmP2 is complementary to the 5' terminus of the P6 adapter and it can initiate synthesis of a first DNA strand that is complementary to the circular adapter nucleic acid-RNA construct including P5 adapter. P6 AmP1 is identical to the 3' terminus of the P6 adapter. Thus, P6 AmP1 is complementary to the first DNA strand synthesized by extending P6 AmP2 and P6 AmP1 can initiate synthesis of a second DNA strand that is complementary to the first DNA strand. Accordingly, primers P6 AmP1 and P6 AmP2 are complementary to different strands of a double stranded nucleic acid sequencing comprising the P6 adapter, where the primer sequences are designed to amplify DNA in opposite directions away from the P6 adapter nucleic acid sequence or its complement.

Figure 6:
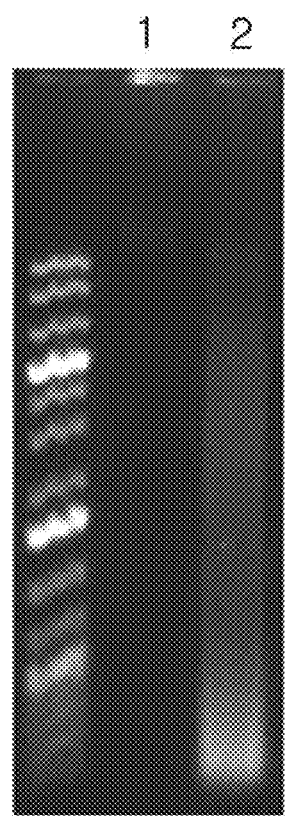
FIG. 6 is an electrophoresis gel image that shows DNA obtained by treating the obtained nucleic acid-RNA fusion construct analyzed in FIG. 5 with polynucleotide kinase (PNK), self-ligating with ligase, and amplifying the circular adapter nucleic acid-RNA fusion construct by a polymerase chain reaction, according to an embodiment of the present invention.

The circular adapter nucleic acid-RNA fusion construct was amplified by multiple displacement amplification (MDA) using the primers of P6 AmP1 and P6 AmP2 to generate double stranded DNA amplification product that includes sequence that is complementary to the circular adapter nucleic acid-RNA fusion construct. The double stranded DNA amplification product was analyzed by electrophoresis as shown in FIG. 6. Lane 1: negative control shows circular adapter nucleic acid-RNA fusion construct before amplification, Lane 2: shows double stranded DNA amplification product. Thus, FIG. 6, Lanes 1 and 2 illustrate nucleic acids before and after amplification by MDA, respectively.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of amplifying RNA in a sample, the method comprising:
   ligating a single-stranded adapter nucleic acid to any one of two ends of RNA in a sample to thereby form an adapter nucleic acid-RNA fusion construct, wherein the adapter nucleic acid-RNA construct consists of the RNA and the single-stranded adapter nucleic acid bound to one end of the RNA;
   self-ligating the adapter nucleic acid-RNA construct to thereby form a circular adapter nucleic acid-RNA fusion construct; and
   amplifying the RNA by incubating the circular adapter nucleic acid-RNA fusion construct together with a first primer and a second primer to thereby form an amplification product,
   wherein when the single-stranded adapter nucleic acid is ligated to the RNA, the first primer comprises a nucleotide sequence that is the same as a continuous nucleotide sequence in the adapter nucleic acid and the second primer comprises a nucleotide sequence that is complementary to a continuous nucleotide sequence in the adapter nucleic acid.

2. The method of claim 1, wherein the sample containing RNA is a biological sample, the sample comprises RNA separated from a biological sample, or the sample comprises a fraction of RNA separated from a biological sample.

3. The method of claim 1, wherein the adapter nucleic acid is DNA or RNA.

4. The method of claim 1, wherein the adapter nucleic acid is DNA and the adapter nucleic acid comprises a restriction enzyme recognition site.

5. The method of claim 1, wherein ligating comprises incubating the adapter nucleic acid to the RNA in the presence of a ligase and wherein self-ligating comprises incubating the adapter nucleic acid-RNA fusion construct in the presence of a ligase.

6. The method of claim 1, wherein amplifying the RNA comprises incubating the circular adapter nucleic acid-RNA fusion construct, the one or more first primers and the one or more second primers in the presence of a polymerase.

7. The method of claim 6, wherein the polymerase is DNA polymerase.

8. The method of claim 7, wherein the DNA polymerase is Bst DNA polymerase, HIV reverse transcriptase, PyroPhage 3173 DNA polymerase, Tth polymerase, BcaBEST DNA polymerase, or a combination thereof.

9. The method of claim 1,
   wherein the adapter nucleic acid lacks a 5' terminal phosphate group,
   wherein the ligating of an adapter nucleic acid to RNA forms an adapter nucleic acid-RNA fusion construct that lacks a 5' terminal phosphate group by ligating the adapter nucleic acid to 5' end of RNA, and
   wherein the method further comprises phosphorylating the 5'-end of the adapter nucleic acid-RNA fusion construct using polynucleotide kinase (PNK) before self-ligating.

10. The method of claim 4, further comprising cleaving the amplification product by incubating the amplification product in the presence of a restriction enzyme that recognizes the restriction enzyme recognition site of the adapter nucleic acid.

11. A method of amplifying an RNA pool in a sample, the method comprising:

ligating a single-stranded adapter nucleic acid to any one of two ends of two or more types of RNA in a sample to thereby form a pool of adapter nucleic acid-RNA fusion constructs, wherein the adapter nucleic acid-RNA construct consists of the RNA and the single-stranded adapter nucleic acid bound to one end of the RNA;

self-ligating each of the adapter nucleic acid-RNA fusion constructs to thereby form a pool of circular adapter nucleic acid-RNA fusion constructs; and amplifying RNA by incubating together the pool of circular adapter nucleic acid-RNA fusion constructs with a first primer and a second primer to thereby form an amplification product, wherein when the single-stranded adapter nucleic acid is ligated to the RNA, the first primer comprises a nucleotide sequence that is the same as a continuous nucleotide sequence in the adapter nucleic acid and the second primer comprises a nucleotide sequence that is complementary to a continuous nucleotide sequence in the adapter nucleic acid.

12. The method of claim 11, wherein the sample containing RNA is a biological sample, the sample comprises RNA separated from a biological sample, or the sample comprises a fraction of RNA separated from a biological sample.

13. The method of claim 11, wherein the adaptor nucleic acid is DNA or RNA.

14. The method of claim 11, wherein the adaptor nucleic acid is DNA and the adapter nucleic acid comprises a restriction enzyme recognition site.

15. The method of claim 11, wherein the ligating comprises incubating the adapter nucleic acid to the RNA in the presence of a ligase and the self-ligating comprises incubating the adapter nucleic acid-RNA fusion construct in the presence of a ligase.

16. The method of claim 11, wherein amplifying the RNA comprises incubating the circular adapter nucleic acid-RNA fusion construct, the one or more first primers and the one or more second primers in the presence of a polymerase.

17. The method of claim 11, wherein the polymerase is DNA polymerase.

18. The method of claim 17, wherein the DNA polymerase is Bst DNA polymerase, HIV reverse transcriptase, PyroPhage 3173 DNA polymerase, Tth polymerase, BcaBEST DNA polymerase, or a combination thereof.

19. The method of claim 11,
wherein the adapter nucleic acid lacks a 5' terminal phosphate group,
wherein the adapter nucleic acid-RNA fusion construct is formed by ligating the adapter nucleic acid to 5' end of RNA, and
wherein the method further comprises phosphorylating 5'-end of the adapter nucleic acid-RNA fusion construct by PNK before self-ligating.

20. The method of claim 14, further comprising cleaving the amplification product by incubating the amplification product in the presence of a restriction enzyme that recognizes the restriction enzyme recognition site of the adapter nucleic acid.

* * * * *